United States Patent [19]

Enomura et al.

[11] Patent Number: 5,772,929
[45] Date of Patent: Jun. 30, 1998

[54] MANUFACTURING METHOD OF MICROCAPSULE USING PHOSPHOLIPID

[75] Inventors: Shinichi Enomura, Kashihara; Mitsuru Nakano, Sakai, both of Japan

[73] Assignee: M Technique Co., Ltd., Osaka, Japan

[21] Appl. No.: 560,815

[22] Filed: Nov. 20, 1995

[30] Foreign Application Priority Data

Jul. 10, 1995 [JP] Japan .................................... 7-198191

[51] Int. Cl.⁶ .............................. B01J 13/00; B01J 13/04
[52] U.S. Cl. ......................................... 264/4.1; 427/213.3
[58] Field of Search .......................... 264/4.1; 427/213.3

[56] References Cited

U.S. PATENT DOCUMENTS

| | | | |
|---|---|---|---|
| 4,350,607 | 9/1982 | Apfel | 252/408 |
| 4,532,130 | 7/1985 | Djordjevich et al. | 424/101 |
| 4,634,590 | 1/1987 | Cohen et al. | 424/88 |
| 5,324,436 | 6/1994 | John et al. | 210/638 |
| 5,340,860 | 8/1994 | Brake et al. | 524/166 |
| 5,457,182 | 10/1995 | Wiederrecht et al. | 530/402 |
| 5,508,341 | 4/1996 | Mayer et al. | 524/596 |

*Primary Examiner*—Jeffrey C. Mullis
*Attorney, Agent, or Firm*—Birch, Stewart, Kolasch & Birch

[57] ABSTRACT

The invention relates to a method of manufacturing microcapsules (fat emulsion or liposome) of high stability and smaller mean particle size with a smaller energy and in a shorter treating time. Prior to dispersing a phospholipid treating liquid in a high speed rotary dispersing machine, a treating tank of the high speed rotary dispersing machine is filled up with only the treating liquid. Dispersion of the treating liquid is conducted by rotating at high speed while the treating tank is pressurized to reduce cavitation generation. For precision dispersion of this treating liquid, it is transferred into a precision dispersion apparatus, such as high pressure homogenizer, without contacting with a gas phase. The method reduces the mean particle size of the microcapsules to increase their stability for a long time period.

14 Claims, 3 Drawing Sheets

MANUFACTURING METHOD OF MICROCAPSULE USING PHOSPHOLIPID

BACKGROUND OF THE INVENTION

The present invention relates to a manufacturing method of microcapsule using phospholipid (fat emulsion or liposome).

Today, microcapsules using phospholipid (emulsion or liposome) are used in medicines, other chemicals, cosmetics, functional foods and others, and they are generally manufactured by preliminary dispersing machine and precision dispersing machine. As the preliminary dispersing machine, a high speed rotary dispersing machine is most widely used, while a high pressure homogenizer is used as precision dispersing machine. FIG. 3 is a conceptual diagram of a manufacturing apparatus comprising a high speed rotary dispersing machine 101 and a high pressure homogenizer 201, in which a treating object is charged into the high speed rotary dispersing machine 101, and blades 103 are rotated at high speed to disperse preliminarily the dispersed phase into the continuous phase of the treating object. The preliminarily dispersed treating object is sent into the high pressure homogenizer 201 through a pump 301, and a dispersed precisely, and thereby the preparation is complete. Meanwhile, the treating object taken out of the high pressure homogenizer 201 may be put back into the high speed rotary dispersing machine 101 as in the drawing, or may be passed only in the high pressure homogenizer 201 several times.

In the case of liposome, as the treating object, a continuous phase containing water and/or water-soluble chemical, and a dispersed phase containing phospholipid and/or fat-soluble chemical are used. In the case of fat emulsion, as the treating object, a continuous phase containing water and/or water-soluble component, a dispersed phase containing oil and/or fat-soluble chemical, and a surface active agent containing phospholipid are used.

In preliminary dispersion, these treating objects s are charged to a proper liquid level in the treating tank 102 of the high speed rotary dispersing machine 101, and blades 103 are rotated at high speed to apply shearing force by rotation of blades to the treating objects, thereby dispersing and processing. On the other hand, precision dispersion is a process of dispersion by applying high voltage to the preliminarily dispersed treating objects, and in order to obtain microcapsules (fat emulsion or liposome) of target mean particle size, it is repeated several to scores of times by the high pressure homogenizer 201.

Incidentally, microcapsules (fat emulsion or liposome) are often preferable from the viewpoint of function in the body when the particle size is smaller, but to reduce the particle size, it has been said that it is necessary to apply a larger energy to the treating objects. More specifically, to obtain microcapsules (fat emulsion or liposome) of smaller particle size, the pressurizing pressure by the high pressure homogenizer must be heightened, and the treating times by the high pressure homogenizer must be increased. To obtain microcapsules (fat emulsion or liposome) of smaller particle size, it has been attempted to raise the concentration of surface active agent containing phospholipid or increase the pressurizing pressure or treating times, but it is substantially impossible to obtain mean particles size of 150 nm or less in the existing system of fat emulsion with phospholipid concentration of about 1.2% and oil and fat of 10% or more.

Moreover, to enhance the stability of microcapsules (fat emulsion or liposome) of this type or products (medicines, other chemicals, cosmetics, functional foods, etc.) using such microcapsules (fat emulsion or liposome), it has been considered necessary to reduce the mean particle size of the microcapsules (fat emulsion or liposome). That is, in the case of microcapsules (fat emulsion or liposome) with relatively large mean particle size, separation occurs easily due to aging effects, and to improve this, it has been believed necessary to apply a larger energy to the treating objects to decrease the mean particle size of microcapsules (fat emulsion or liposome).

It is hence an object of the invention to present a method of manufacturing microcapsules (fat emulsion or liposome) of desired mean particle size, with smaller energy than in the prior art (specifically, with the force applied to the treating object by the blades of high speed rotary dispersing machine or force applied to the treating object by precision dispersing machine such as high pressure homogenizer), and in a shorter treating time.

In other words, it is an object to present a method of manufacturing microcapsules (fat emulsion or liposome) of smaller means particle size when the applied energy (specifically, the force applied to the treating object by the blades of high speed rotary dispersing machine or force applied to the treating object by precision dispersing machine such as high pressure homogenizer) and treating time are same as in the conventional method.

It is other object of the invention to present a method of manufacturing microcapsules (fat emulsion or liposome) high in stability for a long period. More specifically, in comparison with microcapsules (fat emulsion or liposome) manufactured by a conventional method, if compared at same mean particle size or same magnitude or time of energy applied, it is an object to present a method of manufacturing microcapsules (fat emulsion or liposome) enhanced in stability as compared with prior art in either case.

It is a different object of the invention to present a method of manufacturing microcapsules (fat emulsion or liposome) smaller in mean particle size and higher in stability, as compared with microcapsules (fat emulsion or liposome) manufactured by a conventional method.

BRIEF SUMMARY OF THE INVENTION

The prior art has been improving the subjects of reduction of mean particle size or enhancement of stability, mainly with the energy applied to the treating object, while the invention is intended to take note of hitherto ignored bubbles, in particular, tiny bubbles not recognized by the eye, in solving the problems of the prior art. That is, the problems are solved by presenting a manufacturing method of microcapsule using phospholipid, comprising a step of dispersing a treating object by means of a high speed rotary dispersing machine, by using phospholipid at least as one type of treating object, wherein the treating tank of the high speed rotary dispersing machine is filled up with the treating object only, and dispersion is effected by high speed rotation with the treating tank under pressure with the treating object.

By executing the invention, bubbles, especially tiny bubbles can be eliminated or suppressed, and hence problems associated with bubbles, especially tiny bubbles, are eliminated or decreased, and the problems can be solved.

By reviewing the prior art form the viewpoint of bubbles, especially tiny bubbles, in the case of preliminary dispersion by using the high speed rotary dispersing machine 101, cavitation occurs in the high speed rotating parts of blades 103, rotary shaft 4 and others, and dissolved gas in the treating objects s forms bubbles. At the same time, bubbling is vigorous by inclusion of atmosphere (vapor phase k above treating objects s in the treating tank 102). These bubbles are, as a matter of course, transformed into tiny bubbles by the dispersing action, and are hardly recognized by the eye.

Such tiny bubbles (including gas molecules such as $O_2$ and $N_2$) may be present as being stabilized by phospholipid. As this mechanism, the following hypothesis may be considered.

That is, the tiny bubbles may be taken into or adsorbed in the follicles of phospholipid or its membrane.

Once falling in this state, if energy is applied from outside for the purposes of dispersing, energy is absorbed by volume changes of bubbles, and it is hard to obtain target particle size. More specifically, tiny bubbles coexist with oil in aqueous solution, and if energy is applied from outside, the energy is easily absorbed, not acting as energy for dispersion.

The existence of such tiny bubbles cannot be distinguished visually, and, as stated above, it has been mainly intended to improve from the viewpoint of energy to be applied to the treating object, and the improvement taking note of bubbles has been limited to removal of large visible bubbles generated in the stage of preliminary dispersion, or the empirical technique of waiting until bubbles subside and then starting precision dispersion. Such improvement ignoring the tiny bubbles is far from radical solution, and in other words, while ignoring the problem of applying the energy effectively to the treating object, only by merely increasing the pressurizing pressure by the high pressure homogenizer or by repeating the same process many times, only a slight improvement was obtained at the sacrifice of energy loss.

Incidentally, if tiny bubbles coexist with oil in aqueous solution, the interface area increases, and hence a larger volume of surface active agent is needed.

Moreover, in the treating object obtained in such process, tiny stable bubbles are mixed in, and they seem to have effect on long-term stability of the treating object. For example, as the mechanism, the problems are formation of ascending stream for a long time (several hours to several months) by tiny bubbles, and oxidation by oxygen in bubbles.

By contrast, in the invention, entry or generation of bubbles is prevented in preliminary dispersion by high speed rotary dispersing machine. That is, the treating tank of the preliminary dispersing machine is filled up with the treating objects only, and there is no gas phase substantially, and thereby preventing entry of air. More importantly, when rotating the blades at high speed, by performing under pressure of the treating objects, bubbling of dissolved gas by cavitation is prevented (substantially eliminated or decreased). Accordingly, formation of tiny bubbles is prevented, and the applied energy can be effectively utilized in the treating objects, so that the desired purpose is achieved. In the treating objects thus obtained in the method of the invention, tiny stable bubbles are not contained or very few, the ascending stream mentioned above is hardly formed, and the treating objects are stable for a long period. Still more, the problem of oxidation by air in the bubbles hardly occurs. As a result of decrease of the amount of existence of tiny bubbles, moreover, the interface area is smaller and hence the required amount of surface active agent is saved.

The high speed rotary dispersing machine used in the invention is a dispersing machine for forming cavitation by rotation at ordinary temperature and ordinary pressure, and more specifically high speed rotary dispersing machines of various type cans be used, such as dissolver type, homomixer type, and comb type. Filling of the treating tank of the high speed rotary dispersing machine with the treating objects only is intended to avoid contact with gas phase as far as possible, and if there is a slight gas phase, it is permissible as far as the existing amount of tiny bubbles can be decreased. The pressurization of the treating tank by treating objects is enough at a level slightly higher than the ordinary pressure so as to decrease generation of cavitation, or 0.1 $kg/cm^2$ or more, or more preferably 0.3 $kg/cm^2$ or more, but it may be variable depending on the rotating speed and treating temperature.

As the treating objects of the invention, in the case of liposome, a continuous phase containing water and/or water-soluble chemical, and a dispersed phase containing phospholipid and/or fat-soluble chemical may be used. In the case of fat emulsion, as the treating objects, a continuous phase containing water and/or water-soluble component, a dispersed phase containing oil and/or fat-soluble chemical, and a surface active agent containing phospholipid may be used. Examples of phospholipid (lecithin) include yolk phospholipid and soybean phospholipid. Examples of water-soluble or fat-soluble chemicals include antibiotics, chemotherapeutic agents, antiallergic agents, cardiovascular remedies, anti-inflammatories, antirheumatic agents, hormones, vitamins, malignant tumor remedies, contrast medium, diagnostic medicines, other pharmaceutical components, agricultural chemicals, cosmetics, and active ingredients in functional foods. Examples of oil include soybean oil, olive oil, other natural oils, and synthetic oils.

Only by processing by the high speed rotary dispersing machine in the above conditions, a manufacturing method of microcapsules using phospholipid is realized, but it may be also accompanied by precision dispersion by high pressure homogenizer or ultrasonic homogenizer. In this case, the material treated by the high speed rotary dispersing machine is transferred into the precision dispersing apparatus without contacting with gas phase to perform precision dispersion, so that entry of fresh bubbles due to contact with gas phase is prevented.

As the pretreatment, the treating object may be stirred in advance. In this case, the blades are rotated at low speed during stirring, and there is no problem of cavitation due to high speed rotation as in the case of dispersion process.

In batch operation, meanwhile, the treating object is put into the treating tank of the high speed rotary dispersing machine, and is stirred by rotating at low speed. In this case, too, since the blades are rotated at low speed during stirring, there is no problem of cavitation due to high speed rotation as in the case of dispersion process, and bubbles can be removed from the air when charging the powder. To this stirred treating object, an other treating object may be added if necessary, and the dispersion process is further conducted by high speed rotation.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

Embodiments of the invention are described in detail below together with comparative examples.

First referring to embodiment 1 and comparison 1, the difference in the reaching particle size in air mixture and time-elapsed stability is discussed.

Figure 1:
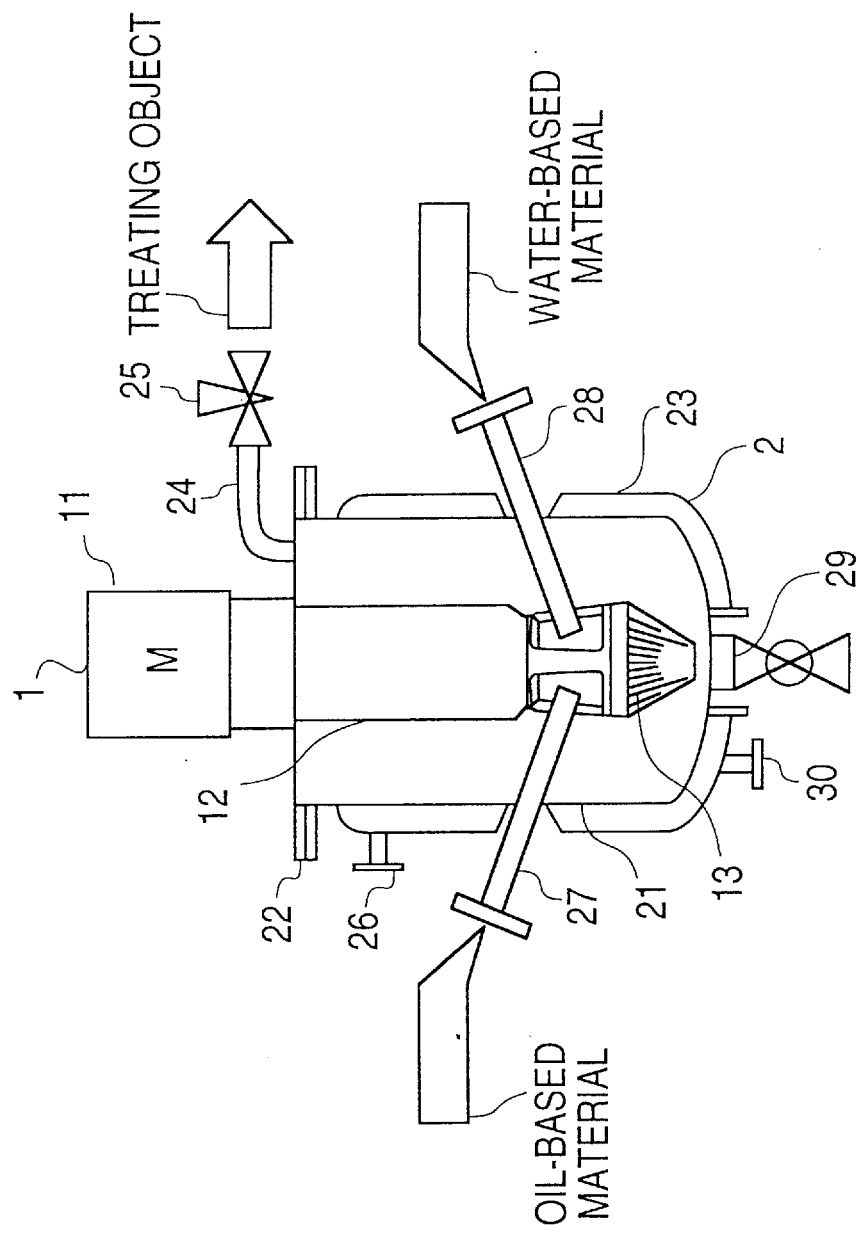
FIG. 1 is a internal structural explanatory diagram of a manufacturing apparatus in an embodiment of the invention.

Explaining the apparatus used in the embodiment, as shown in FIG. 1, a high speed rotary dispersing machine 1 is installed in a pressurized tank 2. This high speed rotary dispersing machine 1 is Clear Mix CLM-0.8S made by M Technique Co. Ltd. The high speed rotary dispersing machine 1 has a motor 11 in its upper part, and its rotary shaft (not shown) droops downward, and it is designed to disperse by rotation of rotary blades (not shown) at its lower end. On the outer circumference of the rotary shaft, a cylinder 12 is mounted, and a screen 13 is attached to the lower end of the cylinder 12. The treating object is dispersed between the rotary blades and screen 13 by rotating of the rotary blades.

The treating tank 2 has a tubular main body 21 having a bottom, and a lid 22 is fitted to its open end so as to enclose tightly, and it has a durability to withstand pressurization. A jacket 23 is provided on the outer circumference of the main body 21, and by passing warm water or cool water into the jacket, the temperature in the treating tank main body 21 is adjusted. In the upper part or lid (lid in this embodiment) of the treating tank main body 21, a treating object outlet 24 is provided, and this outlet 24 is furnished with a device for adjusting the pressure of the treating object in the treating tank 2 such as needle valve 25. Moreover, in the upper part or lid of the treating tank main body 21 (the upper part of the treating tank main body 21 in this embodiment), an exhaust port 26 is formed, and an intake device such as vacuum pump (not shown) is connected to the exhaust port 26. In the middle of the treating tank main body 21, a charging inlet of treating object is provided. In this embodiment, an inlet for oil-based material 27 and an inlet for water-based material 28 are provided. A drain cock 29 is formed in the bottom of the treating tank main body 21, and an insertion port 30 for thermometer or other measuring device is formed in its vicinity.

TABLE 1

| Prescription of treating object (liposome) | |
|---|---|
| Phospholipid | 5.0 wt % |
| (yolk lecithin PL-100P, made by Kewpie Co.) | |
| Refined water | 94.5 wt % |
| 2-Phenoxy ethanol | 0.5 wt % |
| The experiment scale is 355 g. | |

The treating object prescribed in Table 1 was preliminarily dispersed in the high rotary dispersing machine.

In this preliminary dispersion, at ordinary temperature and atmospheric pressure (open), the high speed rotary dispersing machine 1 was operated for 5 minutes at 10,000 rpm. That is, the treating tank 2 was the one shown in FIG. 1, but without enclosing it, preliminary dispersion was conducted at atmospheric pressure (open). After preliminary dispersion, the treating object (prescription) is evacuated to remove bubbles, and this evacuated treating object (prescription) is supposed to be sample A.

<Embodiment 1>

Dispersion is processed by using the apparatus shown in FIG. 1. The treating tank 2 was smaller than the one used in preliminary dispersion. By enclosing the treating tank 2, sample A was charged into the treating tank 2 so that bubbles may not be left over inside, and the treating tank 2 was 100% sealed with sample A liquid. At 20,000 rpm rotating speed of the high speed rotary dispersing machine 1, when the temperature reached 70° C., the operation was continued for 5 minutes. At the same time, the pressure in the treating tank 2 was adjusted to 1 $kg/cm^2$ to 1.5 $kg/cm^2$. By passing cooling water into the jacket 23 for 5 minutes, the sample A liquid was cooled to 30° C. in a short time. The rotating speed was properly adjusted, and the machine was stopped when reaching 30° C., and the sample A liquid was taken out from the outlet 24. This is embodiment 1.

<Comparison 1>

When dispersing by using the apparatus shown in FIG. 1, the sample A liquid was charged while leaving air in the treating tank 2, and the sample A liquid and air were sealed in the treating tank 2. Dispersing in the same conditions as in embodiment 1, the sample A liquid was taken out of the outlet 24. This is comparison 1.

Thus, embodiment 1 was fabricated in the condition of suppression of generation of tiny bubbles, while comparison 1 has effects of tiny bubbles by generation of cavitation or inclusion of residual air. By gross observation, there was no difference between embodiment 1 and comparison 1.

[Vacuum Test]

Embodiment 1 and comparison 1 were transferred into individual containers, and the containers were evacuated by vacuum pump, and the remaining state of air (bubbles) taken in embodiment 1 and comparison 1 was inspected. As a result, the liquid level was not changed in embodiment 1 liquid, but the liquid level rose significantly in comparison 1 liquid. In embodiment 1, tiny bubbles were not recognized, whereas in comparison 1, existence of tiny bubbles due to inclusion of residual air in the tank and generation of cavitation was confirmed.

[Measurement of Particle Size and Standard Deviation, and Long-Term Stability]

In sample A of embodiment 1 and comparison 1 evacuated in the above procedure, the particle size and standard deviation were measured by means of particle size distribution meter Zeta Plus of Brook Haven, and also two-weak stability was studied by measuring the particle size and standard deviation after leaving in a thermostatic oven at 50° C. for 2 weeks. The results are shown in Table 2. As clear from Table 2, in embodiment 1, obviously as compared with sample A and comparison 1, the particle size was small, the particle size distribution was uniform, and the stability was high. It is thus proved that presence or absence of air entry has a critical effect on the reaching particle size and stability of microcapsule using phospholipid.

TABLE 2

|  | First day | | 2 weeks later | |
|---|---|---|---|---|
|  | Particle size | Standard deviation | Particle size | Standard deviation |
| Sample A | 450 nm | 0.415 | Separated | |
| Embodiment 1 | 75 nm | 0.15 | 75 nm | 0.17 |
| Comparison 1 | 180 nm | 0.210 | Separated | |

Referring now to embodiments 2 to 5 and comparisons 2 to 6, effects of air entry are discussed in the case of dispersion process by high speed rotary dispersing machine followed by precision dispersion by precision dispersion apparatus.

TABLE 3

| Prescription of treating object (liposome) | |
|---|---|
| Phospholipid (yolk lecithin PL-100P, made by Kewpie Co.) | 1.2 wt % |
| Refined water | 86.3 wt % |
| Soybean oil | 10.0 wt % |
| Glycerin | 2.5 wt % |
| The experiment scale is 355 g. | |

To form the treating object in Table 3, a phospholipid was dispersed in soybean oil, and heated to 70° C. (oil phase). Glycerin was dissolved in refined water, and heated to 70° C. (water phase). The same high speed rotary dispersing machine 1 as in embodiment 1 was installed in the same treating tank 2, and the oil phase and water phase were charged from the oil-based material inlet 27 and water-based material inlet 28 without admitting air, and the treating tank 2 was filled up with oil phase and water phase only.

At 20,000 rpm rotating speed of the high speed rotary dispersing machine, the operation was continued for 5 minutes while adjusting the pressure within 1 kg/cm$^2$ to 1.5 kg/cm$^2$. This treated liquid is embodiment 2.

The embodiment 2 liquid is introduced into a high pressure emulsifying apparatus micro-fluidizer, a kind of precision dispersing apparatus, without contacting with gas phase, and is treated in the following conditions in the apparatus, and a first pass treated obtain is embodiment 3, a second pass treated object is embodiment 4, and a third pass treated object is embodiment 5.

Figure 2:
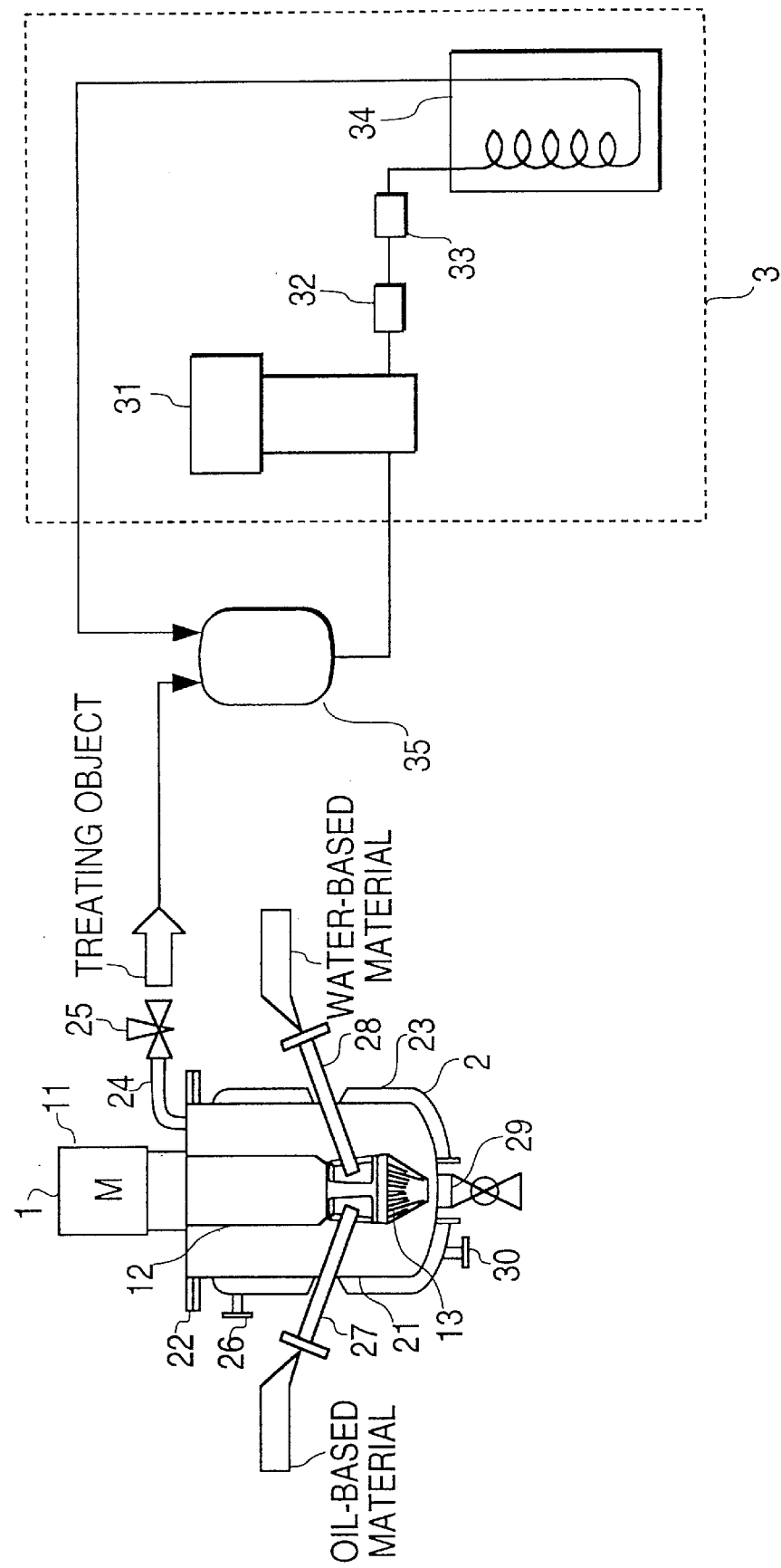
FIG. 2 is its circuit diagram.
Figure 3:
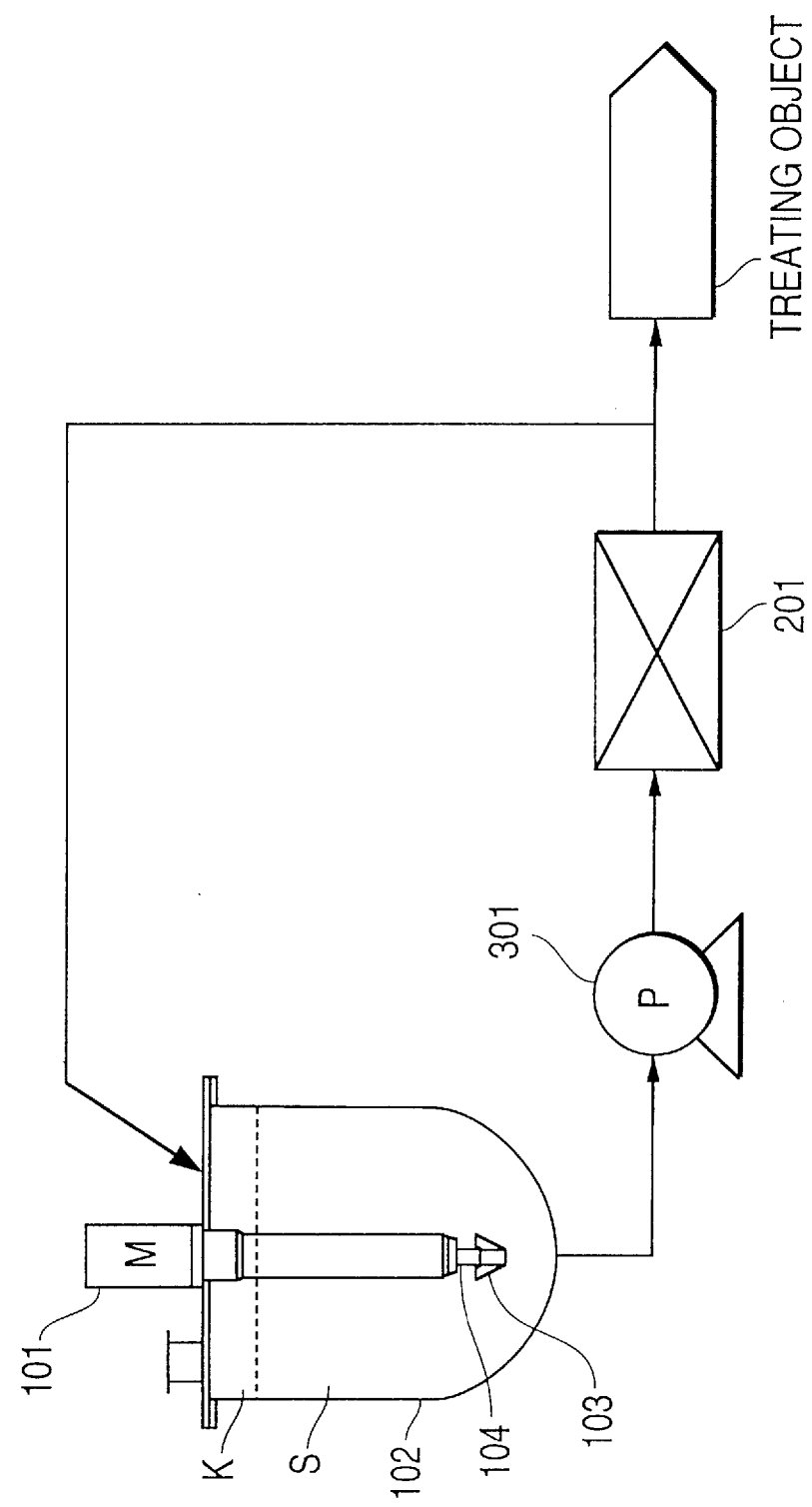
FIG. 3 is a conceptual diagram of a conventional manufacturing apparatus.

The micro-fluidizer is model M-10Y of Micro Fluidics Co. (USA) provided with a cooling device. The pressure was 1400 kg/cm$^2$, and the first pass charging temperature was 70° C., and the first pass take-out temperature was 30° C. After the second pass, the charging temperature and take-out temperature were both 30° C. The micro-fluidizer 3 comprises, as shown in FIG. 2, a high pressure pump 31, an interaction chamber 32, a back pressure module 33, and a cooling device 34, and the high pressure pump 31 and treating object outlet 24 of the treating tank 2 are connected through a charging tank 35. The cooling device 34 and charging tank 35 are connected, and the object after treatment of the first pass is returned to the high pressure pump 31 from the cooling device 34 through the charging tank 35, and undergoes the second pass and on. After the final treatment, the material is taken out of the outlet (not shown) provided in the charging tank 35.

Explaining the comparisons, the treating object in the same prescription as in embodiment 2 is dispersed in the high speed rotary dispersing machine 1, and at this time, by pouring the liquid phase and oil phase into the treating tank 2 together with air, the treating tank 2 was enclosed with oil phase, water phase, and air. The others are same as in the conditions in embodiment 2, and the treated liquid by dispersion process is comparison 2.

In the same procedure and conditions as in embodiments 3 to 5, the liquid is treated in the high pressure emulsifying device micro-fluidizer, and a first pass treated object is comparison 3, a fifth pass treated object is comparison 4, a tenth pass treated object is comparison 5, and a thirtieth pass treated object is comparison 6. The treating conditions of the micro-fluidizer were same as in embodiments 3 to 5, and the first pass charging temperature was 70° C. and the first pass take-out temperature was 30° C. After the second pass, the charging temperature and take-out temperature were both 30 C.

[Particle Size and Standard Deviation]

In embodiments 2 to 5 and comparisons 2 to 6, the particle size and standard deviation were measured by means of particle size distribution meter, Zeta Plus of Brook Haven. The results are shown in Table 4. The figures in parentheses of embodiments and comparisons in Table 4 denote the number of passes of the micro-fluidizer. As clean from Table 4, the dispersion treating method of high speed rotation type by preventing entry of air of the invention was proved to have favorable effects on the reaching particle size of microcapsules using phospholipid produced in the precision dispersion apparatus conducted in later process.

TABLE 4

| | Without air | | With air mixed | | |
|---|---|---|---|---|---|
| | | | Comparison | | |
| Embodiment | Particle size | Standard deviation | (Comparative Example) | Particle size | Standard deviation |
| 2 (0) | 297 nm | 0.127 | 2 (0) | 600 nm | 0.305 |
| 3 (1) | 241 nm | 0.151 | 3 (1) | 342 nm | 0.153 |
| 4 (2) | 180 nm | 0.161 | 4 (5) | 245 nm | 0.162 |
| 5 (3) | 150 nm | 0.124 | 5 (10) | 179 nm | 0.169 |
| | | | 6 (30) | 149 nm | 0.156 |

The invention presents a method of manufacturing microcapsules (fat emulsion or liposome) of desired mean particle size with a smaller energy and in a shorter treating time. In other words, it presents a method of manufacturing microcapsules (fat emulsion or liposome) of smaller mean particle size when the applied energy and treating time are same. The invention further presents a method of manufacturing microcapsules (fat emulsion or liposome) high in stability for a long period.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A manufacturing method of microcapsules comprising the steps of:

filling a treating tank of a high speed rotary dispersing machine with only a treating liquid to avoid contact with a gas phase, said treating liquid comprising at least a phospholipid;

dispersing the treating liquid by the high speed rotary dispersing machine; and while dispersing said treating liquid, pressurizing the treating tank which is kept completely filled or at most has only a slight gas phase to decrease cavitation generation and to form microcapsules, wherein a mean particle size of said microcapsules in said treating liquid is substantially reduced and stability of said microcapsules remains high for a long period as compared to the otherwise identical process but conducted in the presence of an air phase due to the elimination of bubbles in said filling and dispersing steps.

2. The manufacturing method of microcapsules according to claim 1, further comprising the steps of:

stirring a first treating liquid preliminarily at atmospheric pressure; and charging the first stirred treating liquid into the treating tank of the high speed rotary dispersing machine together with a second treating liquid.

3. The manufacturing method of microcapsules according to claim 1, further comprising the steps of:

charging a first treating liquid into the treating tank of said high speed rotary dispersing machine, stirring the first treating liquid by rotating at a speed lower than said high speed for a time period whereby cavitation does not occur;

adding a second treating liquid to the first treating liquid.

4. The manufacturing method of microcapsules according to claim 1, further comprising the steps of:

precisely dispersing said treating liquid by transferring said treating liquid into a precision dispersing high pressure homogenizer, without contacting a gas phase.

5. The manufacturing method of microcapsules according to claim 2, further comprising the step of:

precisely dispersing said first and second treatment liquids by transferring said liquids into a precision dispersing high pressure homogenizer, without contacting a gas phase.

6. The manufacturing method of microcapsules according to claim 3, further comprising the step of:

precisely dispersing said first and second treatment liquids by transferring said liquids into a precision dispersing high pressure homogenizer, without contacting a gas phase.

7. The manufacturing method of microcapsules according to claim 1, wherein the treating liquid comprises a continuous phase containing water and/or a water-soluble chemical, and a dispersed phase containing phospholipid and/or a fat-soluble chemical.

8. The manufacturing method of microcapsules according to claim 2, wherein the second treating liquid comprises a continuous phase containing water and/or a water-soluble chemical, and the first liquid comprises a dispersed phase containing phospholipid and/or a fat-soluble chemical.

9. The manufacturing method of microcapsules according to claim 3, wherein the second treating liquid comprises a continuous phase containing water and/or a water-soluble chemical, and the first treating liquid comprises a dispersed phase containing phospholipid and/or a fat-soluble chemical.

10. The manufacturing method of microcapsules according to claim 4, wherein the treating liquid comprises a continuous phase containing water and/or a water-soluble chemical, and a dispersed phase containing phospholipid and/or a fat-soluble chemical.

11. The manufacturing method of microcapsules according to claim 1, wherein the treating liquid comprises a continuous phase containing water and/or a water-soluble component, a dispersed phase containing oil and/or a fat-soluble chemical, and a surface active agent containing phospholipid.

12. The manufacturing method of microcapsules according to claim 2, wherein the second treating liquid comprises a continuous phase containing water and/or a water-soluble component, and the first treating liquid comprises a dispersed phase containing oil and/or a fat-soluble chemical, and a surface active agent containing phospholipid.

13. The manufacturing method of microcapsules according to claim 3, wherein the second treating liquid comprises a continuous phase containing water and/or a water-soluble component, the first treating liquid comprises a dispersed phase containing oil and/or a fat-soluble chemical, and a surface active agent containing phospholipid.

14. The manufacturing method of microcapsules according to claim 4, wherein the treating liquid comprises a continuous phase containing water and/or a water-soluble component, a dispersed phase containing oil and/or a fat-soluble chemical, and a surface active agent containing phospholipid.

* * * * *

UNITED STATES PATENT AND TRADEMARK OFFICE
CERTIFICATE OF CORRECTION

PATENT NO. : 5,772,929
DATED : June 30, 1998
INVENTOR(S) : Enomura et al.

Page 1 of 1

It is certified that error appears in the above-identified patent and that said Letters Patent is hereby corrected as shown below:

<u>Title page,</u>
Item [75], Inventor, change "Shinichi Enomura, Osaka (JP)" to -- Masakazu Enomura, Osaka (JP) --

Signed and Sealed this

Fifth Day of October, 2004

JON W. DUDAS
*Director of the United States Patent and Trademark Office*